(12) United States Patent
von Recum

(10) Patent No.: US 9,777,106 B2
(45) Date of Patent: Oct. 3, 2017

(54) BISPHENOL POLYMER PRECURSOR REPLACEMENTS

(71) Applicant: CASE WESTERN RESERVE UNIVERSITY, Cleveland, OH (US)

(72) Inventor: Horst A. von Recum, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 88 days.

(21) Appl. No.: 14/775,746

(22) PCT Filed: Mar. 14, 2014

(86) PCT No.: PCT/US2014/027651
§ 371 (c)(1),
(2) Date: Sep. 14, 2015

(87) PCT Pub. No.: WO2014/152714
PCT Pub. Date: Sep. 25, 2014

(65) Prior Publication Data
US 2016/0032043 A1 Feb. 4, 2016

Related U.S. Application Data

(60) Provisional application No. 61/784,261, filed on Mar. 14, 2013.

(51) Int. Cl.
*C08G 59/06* (2006.01)
*C08G 65/38* (2006.01)
(Continued)

(52) U.S. Cl.
CPC ........... *C08G 59/063* (2013.01); *C08G 65/14* (2013.01); *C08G 65/38* (2013.01); *C09D 163/00* (2013.01); *C08K 3/0008* (2013.01); *C08K 5/0008* (2013.01)

(58) Field of Classification Search
CPC ......... C08G 65/14; C08G 59/00–59/72; C08G 65/38; C07D 311/36; C08L 63/00–63/10;
(Continued)

(56) References Cited

U.S. PATENT DOCUMENTS 3,978,027 A * 8/1976 Marshall .............. C08G 59/066
528/104
5,059,640 A * 10/1991 Hegedus ............ C08G 18/4236
523/451

(Continued)

FOREIGN PATENT DOCUMENTS

CN 102161648 A * 8/2011
EP 0739877 A2 10/1996
(Continued)

OTHER PUBLICATIONS

Machine translation of CN 102161648 A.*
(Continued)

*Primary Examiner* — Kregg Brooks
(74) *Attorney, Agent, or Firm* — Tarolli, Sundheim, Covell and Tummino LLP

(57) ABSTRACT

Use of biologically-derived polyphenols for the preparation of epoxy resins is described. Examples of biologically-derived polyphenols include resveratrol, genistein, daidzein, and polyphenols synthesized from tyrosine. Because the epoxy resins are prepared from biologically-derived materials, they provide epoxy resins that will degrade into biologically harmless materials. The epoxy resins can be used to provide coating compositions.

20 Claims, 1 Drawing Sheet

(51) Int. Cl.
*C08L 63/00* (2006.01)
*C09D 163/00* (2006.01)
*C08G 65/14* (2006.01)
*C08K 3/00* (2006.01)
*C08K 5/00* (2006.01)

(58) Field of Classification Search
CPC ... C09D 163/00–163/10; C09J 163/00–163/10
See application file for complete search history.

(56) References Cited

U.S. PATENT DOCUMENTS

| | | |
|---|---|---|
| RE37,160 E | 5/2001 | Kohn et al. |
| 2003/0139610 A1* | 7/2003 | Khare ............... A61K 36/00 549/200 |
| 2007/0135355 A1* | 6/2007 | Bezwada ............ A61L 27/18 434/350 |
| 2011/0237551 A1 | 9/2011 | Okombi et al. |
| 2012/0165429 A1 | 6/2012 | Boutevin et al. |

FOREIGN PATENT DOCUMENTS

| | | | | |
|---|---|---|---|---|
| FR | WO 2010136725 A1 * | 12/2010 | ......... | C08G 59/027 |
| JP | 10182790 A * | 7/1998 | | |
| WO | 2011041487 A1 | 4/2011 | | |

OTHER PUBLICATIONS

Machine translation of JP H10-182790 A.*
Extended European Search Report, Supplementary European Search Report and European Search Opinion for EP Application No. 14770141.1, mailed Sep. 13, 2016, pp. 1-7.
Gupta, Anirban Sen, and Stephanie T. Lopina. "L-tyrosine-based backbone-modified poly (amino acids)." Journal of Biomaterials Science, Polymer Edition 13.10 (2002): 1093-1104.
Harth, Karem C., et al. "Antibiotic-releasing mesh coating to reduce prosthetic sepsis: an in vivo study." Journal of Surgical Research 163.2 (2010): 337-343.
Kohn, Joachim, and Robert Langer. "Poly (iminocarbonates) as potential biomaterials." Biomaterials 7.3 (1986): 176-182.
Kohn, Joachim, et al. "Single-step immunization using a controlled release, biodegradable polymer with sustained adjuvant activity." Journal of immunological methods 95.1 (1986): 31-38.
Sarkar, Debanjan, et al. "Synthesis and characterization of L-tyrosine based polyurethanes for biomaterial applications." Journal of Biomedical Materials Research Part A 90.1 (2009): 263-271.
Thatiparti, Thimma Reddy, Shekharam Tammishetti, and Muram V. Nivasu. "UV curable polyester polyol acrylate/bentonite nanocomposites: synthesis, characterization, and drug release." Journal of Biomedical Materials Research Part B: Applied Biomaterials 92.1 (2010): 111-119.
International Search Report and Written Opinion for PCT/US2014/027651, mailed Jul. 18, 2014, pp. 1-9.
Kohn et al. "Single-step immunization using a controlled release, biodegradable polymer with sustained adjuvant activity." Journal of immunological methods 95.1 (1986): 31-38.

* cited by examiner

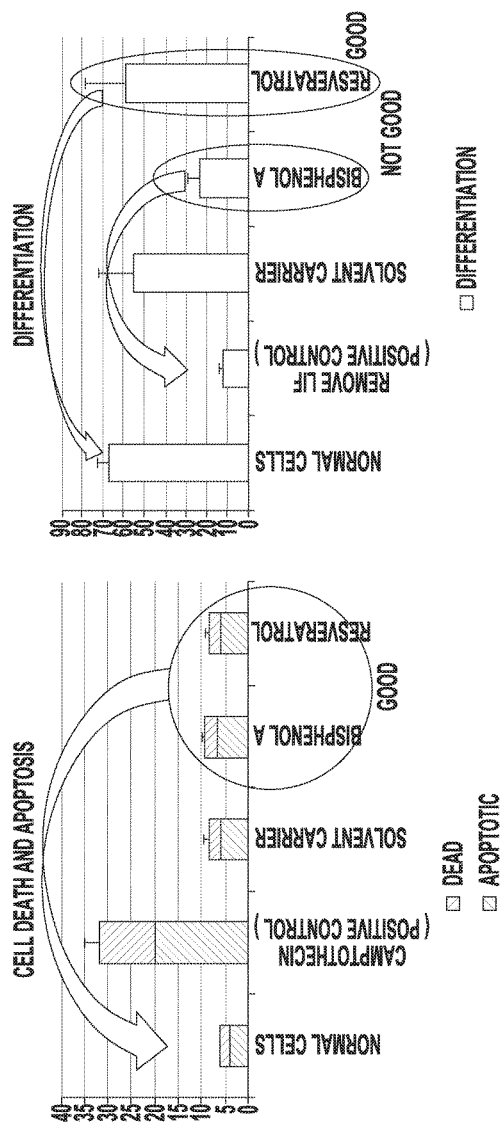

BISPHENOL POLYMER PRECURSOR REPLACEMENTS

RELATED APPLICATIONS

This application claims priority to U.S. Provisional Application Ser. No. 61/784,261, filed on Mar. 14, 2013, which is incorporated herein by reference in its entirety.

BACKGROUND

Current epoxy resins and many other plastics are often prepared using bisphenols, the most common of which is bisphenol A. However, bisphenol A exhibits hormone-like properties that have raised concerns about its suitability in consumer products and food containers. Bisphenol A is thought to be an endocrine disruptor which can mimic estrogen and may lead to negative health effects. More specifically, Bisphenol A closely mimics the structure and function of the hormone estradiol with the ability to bind to and activate the same estrogen receptor as the natural hormone. Since 2008, several governments have questioned its safety, and a 2010 report from the United States Food and Drug Administration (FDA) warned of possible hazards to fetuses, infants, and young children.

Industry has responded to criticism of BPA by creating "BPA-free" products, which are made from plastic containing a compound called bisphenol S (BPS). BPS, which shares a similar structure and versatility to BPA, is now being used in everything from currency to thermal receipt paper, and widespread human exposure to BPS was confirmed in a 2012 analysis of urine samples taken in the U.S., Japan, China and five other Asian countries. However, BPS, like BPA, shares similar problems to BPA in that it has been found to be a hormone disruptor even at extremely low levels of exposure.

A number of investigators have synthesized degradable polymers made from tyrosine and other amino acids and have found that they have high biocompatibility since they are capable of degrading to biologically safe molecules. These polymers are urethanes, carbonates or iminocarbonates synthesized through cyanate based chemistry (another source of potential cytotoxicity). Gupta, A. S. & Lopina, S. T., Journal of biomaterials science 13, 1093-1104 (2002). Kohn, J. & Langer, R., Biomaterials 7, 176-182 (1986). Sarkar et al., Journal of biomedical materials research 90, 263-271 (2009). However there remains a need for bisphenol replacements that can be used as precursors for epoxy resins, and in particular epoxy resins that are safe but not readily degraded.

SUMMARY

Disclosed herein are a variety of biologically-derived compounds suitable for use as bisphenol replacements for the preparation of epoxy resins. Because the bisphenol replacement compounds are biologically derived, epoxy resins prepared from them can be expected to degrade into biologically harmless compounds. Examples of bisphenol replacement compounds include bisphenols prepared from tyrosine, bisphenols prepared from tyramine and coumaric acid, resveratrol, genistein, and daidzein. The bisphenol replacement compounds can be converted to an epoxy resin by converting the free hydroxy groups to glycidyl ethers, which react with one another to form a polymeric epoxy resin. Preferred methods of preparing the epoxy resins are disclosed herein. In some embodiments, the epoxy resin can be included in a coating composition such as a paint which can be used to protect a surface with material that is biologically safe.

BRIEF DESCRIPTION OF THE FIGURES

FIG. 1 provides two graphs comparing the effects of bisphenol A (BPA) and resveratrol on cell death, apoptosis, and cell differentiation. Using the reporter cell line it is clear that BPA interferes estrogen receptor function and therefore negatively impacts cell differentiation. Resveratrol, on the other hand, shows little to no impact on estrogen receptor function and cells differentiation is comparable to negative controls.

DETAILED DESCRIPTION

Unless otherwise defined, all technical and scientific terms used herein have the same meaning as commonly understood by one of ordinary skill in the art to which this application pertains. Although methods and materials similar or equivalent to those described herein can be used in the practice or testing of the exemplary embodiments, suitable methods and materials are described below. In case of conflict, the present specification, including definitions, will control. In addition, the materials, methods, and examples are illustrative only and not intended to be limiting.

Definitions

The terminology as set forth herein is for description of the embodiments only and should not be construed as limiting the application as a whole. Unless otherwise specified, "a," "an," "the," and "at least one" are used interchangeably. Furthermore, as used in the description of the application and the appended claims, the singular forms "a", "an", and "the" are inclusive of their plural forms, unless contraindicated by the context surrounding such.

The recitations of numerical ranges by endpoints include all numbers subsumed within that range (e.g., 1 to 5 includes 1, 1.5, 2, 2.75, 3, 3.80, 4, 5, etc.).

Biologically-derived, as used herein, refers to natural products that are typically obtained from a living source such as an animal, plant, or microorganism. While purification is generally required to isolate the compound from the living source, the compounds are metabolically produced and do not require further chemical modification to obtain the desired compound. While the term biologically-derived indicates that such compounds can be purified in complete form from a living source, it is not meant to imply the exclusion of identical compounds that are prepared through chemical synthesis.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for the compounds of the invention are those that do not interfere with the desired activity of the compounds (e.g., their anticancer activity). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclobutyl, cyclobutylmethyl, cyclopentyl, and cyclohexyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo can also be used alone to indicate an attached halogen atom. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Polymer Precursor Compounds

The inventors have developed a variety of biologically-based polymer precursors useful for the preparation of epoxy resins. These polymer precursors have the advantage of being readily obtained from biological sources, or from the reaction of compounds readily obtained from biological sources. Because these polymer precursors are based on the use of biological compounds that are already known to be safe, they can be used as an alternative to bisphenol compounds to prepare epoxy resins that will not degrade to form products that are known to be a health hazard.

The polymer precursor compounds of the present invention are encompassed by Formula I, Formula II, Formula III, and Formula IV, shown below:

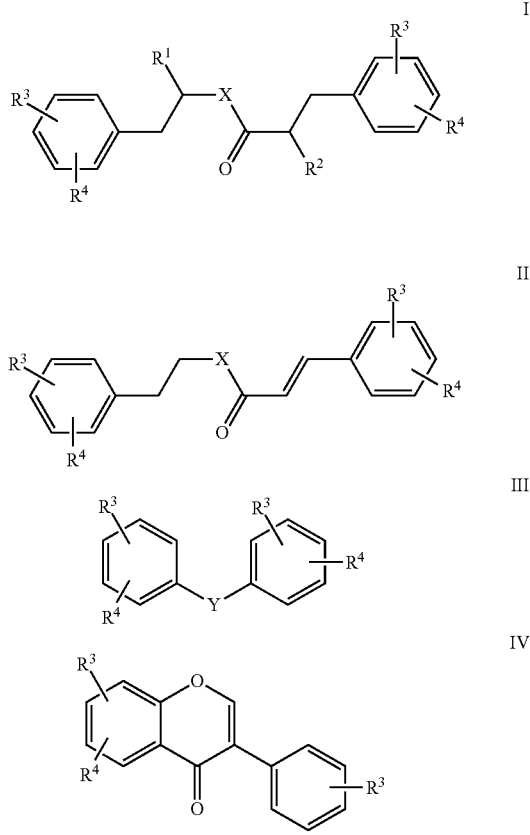

wherein $R^1$ is selected from H and $CO_2R^5$, $R^2$ is selected from H and $NHR^6$, $R^3$ is a hydroxyl or glycidyl ether moiety, $R^4$ is a hydrogen, hydroxyl, or glycidyl ether moiety, $R^5$ is a carboxyl protecting group, $R^6$ is an amine protecting group, X is selected from O and NH, and Y is an ethylene or an ethenylene group.

The polymer precursors of Formulas I-IV all are polyphenols; i.e., compounds that include 2 or more hydroxyl moieties positioned on the phenyl rings. The $R^3$ substituents positioned on the phenyl ring are always either a hydroxyl moiety or a hydroxyl moiety that has been modified to be a glycidyl ether moiety. The $R^4$ substituents, on the other hand, can be either a hydrogen, hydroxyl, or glycidyl ether moiety. Accordingly, depending on the nature of the $R^4$ substituents, the polymer precursors can include 2, 3, or 4 hydroxyl moieties or hydroxyl moieties that have been modified to a glycidyl ether moiety. While including two functional groups is sufficient to allow the compound to be used as a polymer precursor, additional functional groups can be advantageous for the preparation of polymers with increased crosslinking. The hydroxyl moieties or modified hydroxyl moieties can be positioned in any position along the circumference of the phenyl groups. In some embodiments, the hydroxyl moiety or modified hydroxyl moiety is positioned in the para position of the phenyl ring, relative to the alkyl group attached to the phenyl ring.

The hydroxyl moieties positioned along the phenyl groups can be modified to provide glycidyl ether moieties. The hydroxyl groups can be modified to bear glycidyl ether moieties methods known to those skilled in the art, such as reaction with epichlorohydrin. This reaction provides a polymer precursor in which $R^3$ is a glycidyl ether moiety, and $R^4$ is also a glycidyl ether moiety if a hydroxyl moiety was present at the $R^4$ substituent. A glycidyl ether moiety includes an oxirane ring. The oxirane ring can react with the oxirane ring present on other polymer precursors, resulting in formation of an epoxy resin. The size of the polymer found in the resulting epoxy resin depends on the ratio of epichlorohydrin to polyphenol in the initial reaction mixture.

In some embodiments, the polymer precursor is a compound according to Formula I or Formula II. Compounds according to Formula I or Formula II can be obtained through reaction of smaller, biologically obtained dimers such as tyrosine. In some embodiments, the compounds of Formula I or Formula II are defined such that X is NH (a secondary amine). Compounds according to Formula I or Formula II that include an amine are more relatively resistant to degradation and are therefore more stable, but can nonetheless be degraded by digestive proteases within cell endosomes, resulting in the release of biocompatible fragments. For example, in one embodiment of the compounds of Formula I, the polymer precursor can be prepared by the reaction of two tyrosine molecules, to provide a compound having the structure:

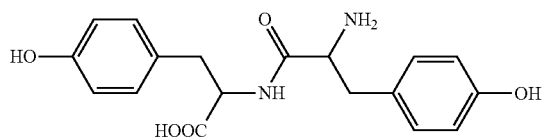 [SMILES: NC(Cc1ccc(O)cc1)C(=O)NC(Cc1ccc(O)cc1)C(=O)O]

To facilitate further reactions, the carboxyl and amine groups can be readily protected to obtain a compound having the structure:

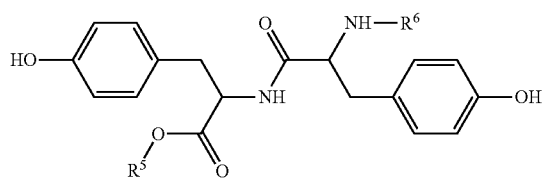

wherein $R^5$ is a carboxyl protecting group and $R^6$ is an amine protecting group. Suitable carboxyl and amine protecting groups are known to those skilled in the art. Examples of suitable amine protecting groups include Fmoc and tBoc, while carboxyl protecting groups include, for example, methyl, ethyl, and t-butyl esters. Suitably protected tyrosine molecules can, for example, be obtained from chemical suppliers such as Sigma-Aldrich®. These compounds can be further reacted to obtain compounds in which the free hydroxyl groups have been modified to glycidyl ethers. Using solid state (protein) synthesis, polymer precursors such as di-tyrosine can be obtained with high yield percentages, and with the amine end protected. The carboxyl end can be easily protected as well, such as through hexyl ester formation. Optimization of protecting groups for the synthesis of tyrosine-based polymers is described by Kohn et al. (J. Immunol. Methods, 95, 31-38 (1986)), the disclosure of which is incorporated herein by reference.

Polymer precursors can also be prepared from compounds other than tyrosine. Examples of such compounds include tyramine, coumaric acid, caffeic acid, dopamine, 4-hydroxyphenylpyruvate, genistein, daidzein, and 3-(4-hydroxyphenyl)-propionic acid. For example, tyramine and p-coumaric acid can be reacted together to provide N-coumaroyltyramine. One advantage of these compounds relative to those derived from tyrosine is that there is no need for protection of free amines or carboxylic acids, since none are present. Another advantage is the presence of a UV-sensitive double bond that can be used to strengthen polymers prepared using the polymer precursor by crosslinking. These compounds (e.g., N-coumaroyltyramine) can also be modified to provide compounds in which the free hydroxyl groups have been modified to glycidyl ethers, as shown by the modified form of N-coumaroyltyramine, below:

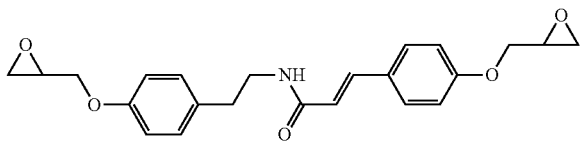

Polymer precursors according to Formula I or Formula II can also be prepared in which X is O. Such compounds can also be prepared through reaction of smaller, biologically obtained dimers, and can be obtained either as polyphenols or as polyphenols modified to bear glycidyl ethers. While the present invention encompasses all of the compounds that are described by Formula I and II, an exemplary compound in which X is O is shown below:

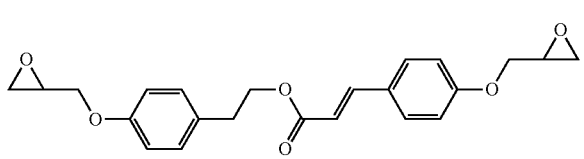 [SMILES: O=C(/C=C/c1ccc(OCC2CO2)cc1)NCCc1ccc(OCC2CO2)cc1]

Another embodiment is directed towards polymer precursor compounds according to Formula III. Unlike the polymer precursor compounds according to Formulas I and II, the polymer precursor compounds according to formula III are not generally obtained through reaction of smaller biologically-derived compounds, but rather are themselves biologically-derived. Formula III is generally based on resveratrol, but can also include polymer precursors based on related compounds such as piceatannol. In addition embodiments, the resveratrol is modified to include hydroxyl groups at different positions along the phenyl rings, or to include a saturated ethylene group (—CH$_2$—CH$_2$—) rather than an unsaturated ethenylene group (—CH=CH—).

One example of a polymer precursor according to Formula III in which Y is an ethenylene group is resveratrol. Resveratrol is a biologically-derived compound, and can be biologically derived from a number of natural sources, including red grapes, peanuts, and Japanese knotweed. Resveratrol can be reacted with epichlorohydrin to provide the polymer precursor compound shown:

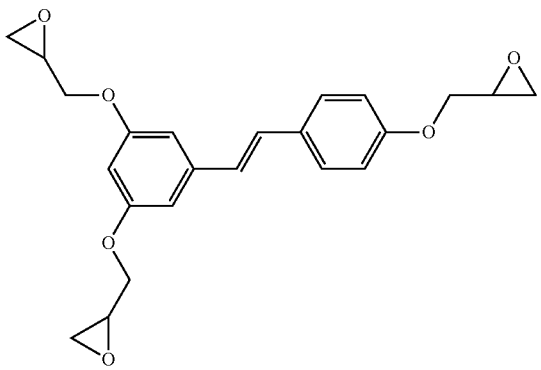 [SMILES: C(=C\c1cc(OCC2CO2)cc(OCC2CO2)c1)/c1ccc(OCC2CO2)cc1]

Resveratrol is a compound according to Formula III in which one of the R$^4$ substituents is a hydroxyl moiety and the other R$^4$ substituent is a hydrogen. Because resveratrol includes more than two hydroxyl groups, resveratrol readily crosslinks when modified to include glycidyl ethers and used to form an epoxy resin. The availability of the UV sensitive double bond of the ethenylene group also provides a site for further crosslinking to strengthen the polymer. However, in some embodiments, it may be preferable to use polymer precursors according to Formula III in which Y is an ethylene group and therefore lacks the double bond.

Another embodiment is directed towards polymer precursor compounds according to Formula IV. As with the polymer precursor compounds of Formulas III, the polymer precursor compounds according to formula IV are not generally obtained through reaction of smaller biologically-derived compounds, but rather are themselves biologically-derived. For example, the compounds genistein and its derivative daidzein are di-phenols are biologically derived, and are available from a variety of natural sources such as soybeans, green beans, and alfalfa sprouts. Genistein and daidzein can be modified to include glycidyl ethers as shown in the structures below (a and b, respectively), which can then be used as polymer precursors for forming an epoxy resin.

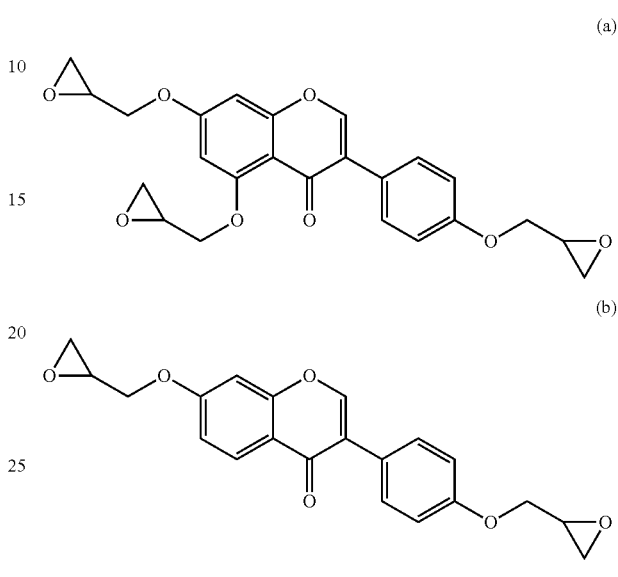

Epoxy Resins

Epoxy resins are polyether resins containing more than one epoxy group capable of being converted into the thermoset form. An epoxy resin forms as a result of the reaction between oxirane groups present on polymer precursor compounds that have been modified to bear two or more glycidyl ethers. While the glycidyl ethers described herein are produced using epichlorohydrin, oxiranes can also be introduced into polymer precursors by oxidation of olefins and oxidation by inorganic peroxides. An example of an epoxy resin is an epoxy resin prepared by the reaction of N-coumaroyltyramine with epichlorohydrin is shown below:

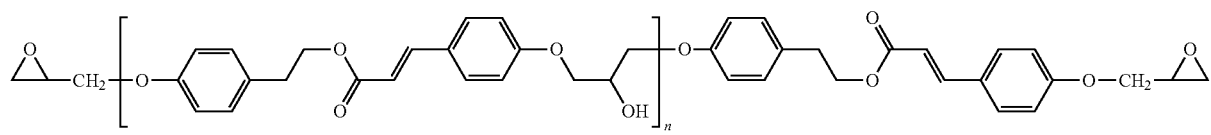

wherein n has a value from 1 to 25.

The term epoxy resin, as used herein, can include any resin or a mixture thereof having two or more epoxy groups, produced by the reaction of an epoxide with polyhydric phenols to produce polyglycidyl ethers. These resins generally have molecular weights in the range of 1,000 to 500,000. The invention also includes modified epoxy resins, in which an epoxy resin forms an adduct with vinyl, acrylic, or polyester resins.

The epoxy resins described herein can be prepared from a compound according to Formula I, II, III, or IV:

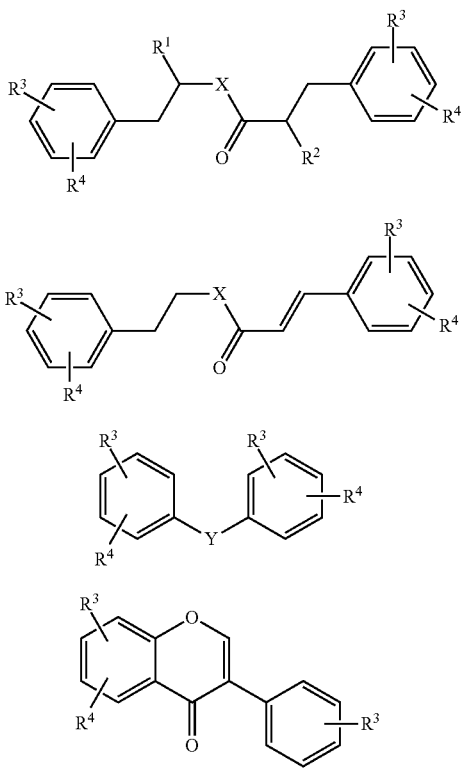

wherein $R^1$ is selected from H and $CO_2R^5$, $R^2$ is selected from H and $NHR^6$, $R^3$ is a glycidyl ether moiety, $R^4$ is a hydrogen or glycidyl ether moiety, $R^5$ is a carboxyl protecting group, $R^6$ is an amine protecting group, X is selected from O and NH, and Y is an ethylene or an ethenylene group. The polymer precursors defined by these formulas differ from the polymer precursors described earlier in that all of these polymer precursors have been modified to include glycidyl ether moieties.

While the epoxy resins are generally prepared from a single polymer precursor, in other embodiments it may be preferable to use two or more different polymer precursors. The additional polymer precursors can be one or more of the polymer precursors described herein. Furthermore, the hydroxyl moieties of $R^3$ and $R^4$ of any of the polymer precursors will have all been modified to be glycidyl ether moieties to allow resin formation. Epoxy resins are normally liquids or have a low molecular weight and are soluble in various aliphatic solvents such as ketones, esters, ether alcohols or any of the aromatic solvents such as xylene, etc.

In some embodiments, the epoxy resin is prepared using a compound according to Formula I or Formula II. For example, in a further embodiment, the epoxy resin is prepared from a compound of Formula I or Formula II wherein $R^4$ is hydrogen and $R^3$ is a glycidyl ether moiety in the para position. In addition, the epoxy resin can also prepared using a compound according to Formula I or Formula II wherein X is NH. These amide containing epoxy resins are relatively resistant to degradation, and while the epoxy resins will degrade under certain conditions into biologically safe degradation products, they are not easily degraded and are considered herein to be non-biodegradable epoxy resins. In contract, in other embodiments, the epoxy resin is prepared using a compound according to Formula I or Formula II wherein X is O. The presence of a readily hydrolysable ester in these compounds renders these epoxy resins much more biodegradable. In yet further embodiments, the epoxy resin is prepared using a polymer precursor compound of Formula III or Formula IV.

The curing of an epoxy resin may occur through homopolymerization between the epoxide compounds themselves, or the conversion of the typically liquid or thermoplastic uncured epoxy resin to a tough thermoset solid epoxy can be brought about by the addition of a curing agent. Curing of an epoxy resin is an exothermic process, and generally results in the shrinking of the epoxy resin. A wide variety of curing agents (also known as hardeners, activators or catalysts) are known to those skilled in the art. These curing agents differ widely in their effect upon the uncured resin, for example, the curing action may be exothermic with some curing agents while requiring the application of external heat with others. Furthermore, the curing epoxy group may react anionically or cationically.

While basic curing agents such as Lewis bases, inorganic bases, primary and secondary amines and amides are most commonly used curing agents, acid curing agents are preferred in many formulations. Of these acid curing agents, carboxylic acid, anhydrides, dibasic organic acids, phenols and Lewis acids are types of curing agents which can be made to successfully bring about the curing reaction.

Amine curing agents include the aliphatic and aromatic amines, and in particular the tertiary amines, $C_2$-$C_{30}$, preferably $C_2$-$C_{10}$ polyamines, polyamides, and amine adducts. The preferred curing agents are the $C_2$-$C_{10}$ polyamines that contain two or more reactive hydrogen groups and amine-terminated polyamide compositions, including those formed through the condensation of unsaturated fatty acids with $C_2$-$C_{10}$ aliphatic polyamines having at least three amino groups per molecule. Examples of amine curing agents include triethylene tetramine, m-phenylenediamine, 3-diethylamino-1-propylamine, Versamid 100, 115, 125, 150 and 1540 resins, ethylene diamine, m-xylylene diamine, 3,3'-iminobispropylamine, tetraethylene pentamine, etc. Linear polyoxypropylene di- or triamines sold as JEFFAMINES® (Huntsman Chemical Co., Austin Tex.) can also be used. Generally a stoichiometric amount or a slight excess of the epoxy resin is employed.

The epoxy resins of the present invention can be used to formulate adhesives, coating compositions, sealing compositions, and fillets. They can be used in bulk, in solvent borne form, with reactive diluents or in aqueous dispersion. Depending on the supply form they are cured with latent curatives, such as dicyandiamide, with solvent borne curatives, or with aqueously dispersed curatives.

If desired, the epoxy resin composition may contain suitable amounts of conventional additives, for example, bulking materials, reinforcing agents, fillers (e.g. coal tar, glass fiber, boron fiber, carbon fiber, cellulose, polyethylene powder, polypropylene powder, quartz powder, mineral silicates, mica, slate powder, kaolin, aluminum oxide trihydrate, aluminum hydroxide, chalk powder, plaster, calcium carbonate, antimony trioxide, bentonite, silica, aerosol, lithopon, baryte, titanium dioxide, carbon black, graphite, iron oxide, gold powder, aluminum powder, iron powder, etc.), pigments, organic solvents (e.g. toluene, xylene, methyl ethyl ketone, methyl isobutyl ketone, ethyl acetate, butyl acetate, etc.), reactive diluents (e.g. butyl glycidyl ether, N,N'-diglycidyl-o-toluidine, phenyl glycidyl ether, styrene oxide, ethylene glycol diglycidyl ether, propylene glycol diglycidyl ether, 1,6-hexanediol diglycidyl ether, etc.), non-reactive diluents (e.g. dioctyl phthalate, dibutyl phthalate, dioctyl adipate, petroleum solvents, etc.), modified epoxy resins (e.g. urethane-modified epoxy resins, rubber-modified epoxy resins, alkyd-modified epoxy resins, etc.), and the like.

Epoxy derivatives of resveratrol and n-coumoryltyramine can be used in paints and coatings similar to bisphenol A based epoxies. Coating compositions could also include a crosslinker. For example, aliphatic amines, cycloaliphatic amines, amidoamines, polyamides, polymercaptans, etc. could be used for ambient temperature cross linking. Materials like boron trifluoride/amine complexes, melamines, anhydrides, aromatic amines, tertiary amines could be used for elevated temperature cross linking. The coating can be applied to a variety of substrates by conventional application methods such a spraying, dipping, brushing, or flow coating. Substrates that can be coated with the composition are, for example, metal, wood, glass, or plastics such as polypropylene, polystyrene, and the like.

In general, the epoxy resins are in solution at concentrations of 40 to 100% solids by weight. Various organic solvents may be used in preparing the coating including xylene, toluene, mineral terpenes, methyl ethyl ketone, methyl isobutyl ketone, ethyl cellosolve, butyl cellosolve, cellosolve acetate, ethyl acetate, butyl acetate, methyl isobutyl carbinol, isopropanol, n-butanol, cyclohexanone or mixtures thereof with various paint solvents in any proportion. Usually, the content of the volatile components i.e. solvents in the coating composition of this invention ranges from about 0 to 50% e.g., 15-35% by weight of the total composition. The amount of solvent may vary depending on the viscosity and method of application of the coating onto the substrate.

Coating compositions used as paints can also include a pigment to providing the coating with a certain color. A wide variety of pigments are known to those skilled in the art. Pigments are often obtained from transition metals, and include pigments based on cadmium, carbon, chromium, cobalt, copper, iron oxide, clay earth, lead, mercury, titanium ultramarine, and zinc.

Coating compositions can also include ultraviolet light stabilizers, antioxidants, catalysts, wetting agents, dispersing or surface active agents, e.g., Anti-Terra-204 (carboxylic acid salts of polyamine-amides), flow modifiers e.g. BYK-320 (polyether modified methylalkyl polysiloxane copolymers), adhesion promoters, etc. Ultraviolet light stabilizers include benzophenones, triazoles, triazines, benzoates, substituted benzenes, organophosphorous sulfides, etc. Coating compositions can also include about 0.01-2.0% by weight, based on the weight of the resin of a curing catalyst. The catalysts are usually organo metallics such as dibutyl tin dilaurate and zinc octoate, tin di-2-ethylhexoate, stannous octoate, stannous oleate, zinc naphthenate, vanadium acetyl acetonate, and zirconium acetyl acetonate.

Compounds of the invention may be synthesized by synthetic routes that include processes similar to those well known in the chemical arts. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.); Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)).

For example, epoxy resins can be prepared by mixing a reactant according to Formula I, II, III, or IV:

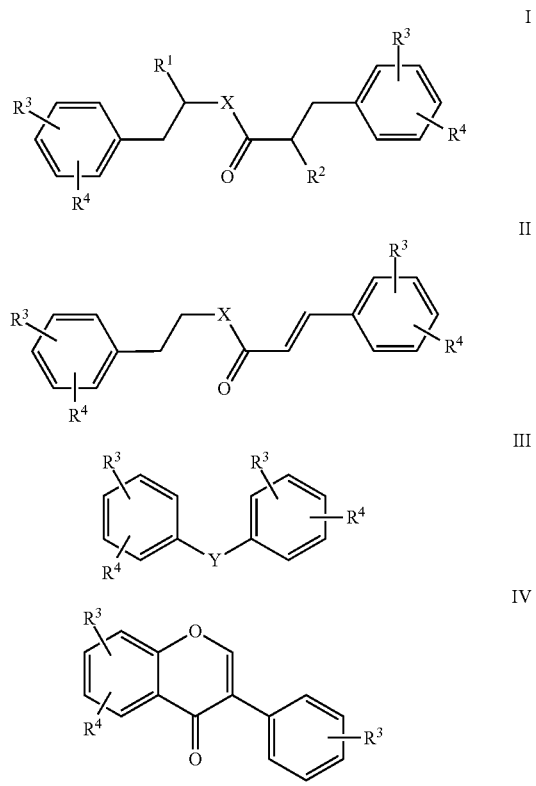

wherein $R^1$ is selected from H and $CO_2R^5$, $R_2$ is selected from H and $NHR^6$, $R^3$ is a hydroxyl moiety, $R^4$ is a hydrogen or hydroxyl moiety, $R^5$ is a carboxyl protecting moiety, $R^6$ is an amine protecting group, X is selected from O and NH, and Y is an ethylene or an ethenylene group, with epichlorohydrin to provide a ratio from about 1:1 up to 10:1 of epichlorohydrine to reactant, heating the mixture to a suitable reaction temperature, and reacting the epichlorohydrin with the reactant of Formula I, II, III, or IV by adding from 1 to 3 equivalents of a NaOH solution having a concentration from about 1 to about 20 weight percent, and purifying the resulting epoxy resin. In some embodiments, the suitable reaction temperature is from about 70° C. to about 90° C.

The present invention is illustrated by the following examples. It is to be understood that the particular examples, materials, amounts, and procedures are to be interpreted broadly in accordance with the scope and spirit of the invention as set forth herein.

EXAMPLES

Example 1: Compare Di-Tyrosine Based Epoxides to Benchmarks

Dimeric versions of tyrosine or derivatives will be reacted with epichlorohydrin as the basis for epoxide chemistry. The resin will be characterized in terms of viscosity, epoxy index (Eq/kg), and compared to a benchmark resin provided.

Synthesis of Precursor, Polymer and Viscosity Characterization

The procedures previously published for epoxide synthesis and characterization will be used to prepare and characterize tyrosine-based polymers. Harth, K. C., et al. The Journal of surgical research 163, 337-343; Nivasu et al., Journal of Biomedical Materials Research Part B-Applied Biomaterials 92B, 111-119 (2010). Briefly, Rheological oscillatory measurements will be performed using a controlled stress rheometer (TA instruments AR2000(ex) rheometer). The geometry used will be stainless steel parallel plate geometry with 12 mm diameter. A solvent trap will be used to prevent evaporation of the solvent. The viscoelastic properties of the water swollen gels will be determined by measuring the changes in the storage modulus, G0, and the loss modulus, G00, at 25° C. by applying a sinusoidal shear stress, s. Two different viscoelastic tests will be performed: (i) stress sweep experiments will be carried out at a constant frequency of 1 Hz, and (ii) a frequency sweep experiment will be performed at a constant stress of 5 Pa (located in the range of linear viscoelasticity) in the frequency range of 0.1-100 Hz. All the rheological measurements will be performed in triplicate and the presented results are the average of those experiments. Apparent polymer network parameters will be obtained from the storage modulus, G0, and will be derived from viscoelastic measurements and the following equations:

$$v_e = \frac{G}{RT\varphi_2^{0.36}} = \frac{E}{3RT\varphi_2^{0.36}}$$

$$M_c = \frac{\rho}{v_e}$$

where G is the shear modulus, $v_e$ is the effective crosslink density, $\phi2$, is the polymer volume fraction, R is the universal gas constant (m$^3$ Pa/K/mol), T is the temperature (K), $\rho$ is the polymer density (kg/m$^3$) (calculated from polymer mass and geometric volume), and Mc is the molecular weight between crosslinks.

Modified Procedure for Determining Epoxy Index, Guo et al., Polymer-Plastics Technology and Engineering, 46, 901-903 (2007)

The procedure for determining the epoxy index includes the following steps: a) Place 150 mL acetone and 5 mL hydrochloric acid into a volumetric flask; b) Weigh 0.4 to 0.5 g polymer and place into a conical bottle, and then add 25 mL hydrochloric acid. Put it into a thermostatic bath (45° C.) for 3.5 h after mixing thoroughly; c) Add 3 drops of indicator into 25 ml hydrochloric acid/acetone solution. First, carry out a blank titration within 30 seconds. The end-point is defined as no color change after 5 seconds. The volumetric amount of NaOH consumed is V$_0$ ml; d) Take the conical bottle and cool to room temperature. Add 3 drops of indicator and carry out titration using NaOH solution. The amount consumed is V ml. 1.4. The epoxy index (EI) is calculated using the following equation:

$$EV = \frac{(V_0 - V)N}{10 W}$$

where N is the concentration of sodium hydroxide solution, mol L$^{-1}$; and W is the mass of polymer.

Example 2: Cell Proliferation, Cytotoxicity, Apoptosis and Differentiation Assays Bisphenols have come under increasing scrutiny due to their capacity to mimic estrogen in biological systems, resulting in numerous health complications. Specifically these effects have been observed in endothelial cell differentiation. Bredhult et al., "Gene expression analysis of human endometrial endothelial cells exposed to Bisphenol A," Reproductive toxicology (Elmsford, N.Y 28, 18-25 (2009). Long et al., Experimental biology and medicine, 226, 477-483 (2001). Accordingly, experiments have been carried out to evaluate the cytotoxicity and differentiation effect of a biologically derived bisphenol polymer precursor replacement. Resveratrol and bisphenol A were incubated with mouse embryonic stem cells and evaluated for cytotoxicity and apoptosis. Cells were then differentiated and evaluated for effect on endothelial differentiation. The results, provided in FIG. 1, show that bisphenol A and resveratrol are relatively indistinguishable with regard to over toxicity using the apoptosis assay, but bisphenol A clearly interferes with estrogen receptor function and therefore negatively effects cell differentiation. Further studies are planned to test further stages of resveratrol epoxidization.

The inventor's lab has developed a mouse embryonic stem cell line capable of providing a quantitative readout of endothelial differentiation due to expression of a green fluorescent protein. Using these and similar cell lines we have been able to assay the effect of new molecules on cell proliferation, death, apoptosis, and endothelial differentiation. Robilotto et al., Dalton Transactions, 40(32): 8083-5 (2011). This cell line will be used to determine the biological effect of the newly proposed polymers as compared to the effect of benchmark controls.

Protocols similar to those previously published can be used to determine the biocompatibility of the new polymers as compared to that of benchmark resin, evaluating the capacity of mouse embryonic stem cells to proliferate, their rate of cell death by toxicity or apoptosis, and their capacity to differentiate into embryonic stem cells. Kim et al., Tissue engineering, 15, 3709-3718 (2009); Kim et al., Tissue engineering, 16, 1065-1074 (2010).

The procedure for testing toxicity was and can be carried out as follows. E14 mouse embryonic stem cells (ATCC.org) are maintained in medium consisting of Dulbecco's Modified Eagle's Medium, 10% fetal bovine serum, and 1% penicillin/streptomycin solution, called D8 medium, and incubated in a humidified incubator at 37° C. and 5% CO$_2$. Initially, a colorimetric cell proliferation assay (MTT assay) is performed to ensure that the new polymer has no overt consequences on cell proliferation. 100,000 E14 cells were added to a 10 cm plate, covered with 1, 10 and 100 mg of polymer sample, and incubated for 48 hours followed by application of the MTT dye solutions and measurement of absorbance at 570 nm.

The number of apoptotic cells are quantified using an annexin-V apoptosis staining kit with 7-Amino-actinomycin D (7-AAD) vital stain (AnnexinV—PE Apoptosis Detection Kit; BD Biosciences Pharmingen, San Diego, Calif.). Cytometric analysis is performed on a FACSCalibur (Becton-Dickinson, San Jose, Calif.). The excitation wavelength is 488 nm, and emission was collected on channel FL2 (564-601 nm) and 7-AAD on FL3 (670-nm long pass filter). Microscopy images can be obtained from a Nikon Eclipse TE300 microscope using a QImaging Retiga-SRV Fast 1394 camera and Image-Pro 6.2 software.

Into a six-well culture plate 1.0 mL of D8 medium containing about 100,000 E14 cells is added. This mixture is allowed to stand for one hour for the cells to attach to the plate. A 1, 10, or 100 mg polymer sample is then added to individual wells. The cell culture plate is then incubated at 37° C. and 5% $CO_2$ concentration for 72 hours. The cells will then be trypsinized and re-suspended in 200 µL of 1× annexin V binding buffer and 100 µL of this solution is transferred to a 3 mL culture tube. Annexin V-PE (5.0 µL) and 5.0 µL of 7-amino-actinomycin stain is added and the suspension is be gently mixed and then incubated at room temperature in the dark for 15 minutes. A 500 µL-aliquot of 1× annexin V binding buffer is added and the culture tube and gentle mixing and fluorescence-activated cell analysis is then performed.

Example 3: Synthesis of N-Coumaroyltyramine Based Epoxy Resin

Synthesis of N-coumaroyltyramine:
N-coumaroyltyramine was prepared using the following materials: P-Coumaric acid, tyramine, 1,3-diisopropylcarbodiimide (DIC), dichloromethane (DCM), and N,N-dimethylformamide (DMF). 2 g of P-Coumaric acid was dissolved in 200 ml dichloromethane (DCM), in a two necked round bottomed flask fitted with a nitrogen bubbler. After 1 hour stirring, 1.5417 ml of 1,3-diisopropylcarbodiimide was added drop wise and stirred for another 18 hours at room temperature. In a separate round bottomed flask, 2.1721 g of tyramine was dissolved in 50 ml of N,N-dimethylformamide (DMF). Tyramine solution was added to the reaction mixture and stirred gently for 2 hours. The excess DCM was removed from the mixture by evaporation. Then the synthesized product was precipitated by the adding of water. The precipitated material was then washed with ethyl acetate and 5% $NaHCO_3$ solution and dried the product at room temperature. The product was characterized by NMR and FTIR.

FTIR of N-coumaroyltyramine: The sample was prepared by grinding with potassium bromide (KBr) and compressed to obtain a thin pellet. Scans were run from 4000 to 400 $cm^{-1}$. The FTIR analysis of the N-cumaroyltyramine showed the typical signals corresponding to the formation of the amide bond between p-coumaric acid and tyramine. The absorption bands were found around 3322 $cm^{-1}$ (vOH and v-NH), 1665 $cm^{-1}$ (C=O), 1620 $cm^{-1}$ (C=C), 1560-1600 $cm^{-1}$ (CONH), 700-800 $cm^{-1}$ (aromatic groups). Both the presence of amide as well as C=C in the FTIR spectra indicated that the reaction had been successful.

$H^1$ NMR: $^1$H NMR analysis demonstrated the characteristic peaks of C=C found in between δ 5 and 6. The double bond peaks are suppressed due to noise of the spectra. The amide proton observed at δ 7.94 and aromatic protons were found between 6.74 to 7.44. The presence of double bond and amide proton in the NMR spectra indicates the formation of N-coumaroyltyramine.

Synthesis of Epoxy Resin:
0.5 g of N-coumaroyltyramine and 0.559 ml of epichlorohydrin were taken in a three necked round bottomed flask fitted with an over head mechanical stirrer, dropping funnel and a condenser. The contents were heating at 80° C. in an oil bath. 0.1 N NaOH was added dropwise over a period of 3 hrs through dropping funnel. After complete addition of NaOH, the reaction mixture was stirred for 4 hrs at 80° C. The unreacted epichlorohydrin was removed by distillation method at 180° C. under reduced pressure. The formed NaCl salt was washed with little warm water. The product was characterized by $H^1$ NMR.

$H^1$ NMR: $^1$H NMR analysis demonstrated the characteristic peaks of C=C found in between δ 5 and 6 as small shoulder which was present in the $^1$H NMR of N-coumaroyltyramine. The double bond was not affected by epoxidation. The double bond peaks are suppressed due to noise of the spectra. The amide proton observed at δ 7.94 and aromatic protons were found between 6.74 to 7.44. A multiplet appeared near 2.75-2.91 corresponded to —$CH_2$ (a) group of epoxy ring. A singlet and a multiplet appeared at 3.5-3.65 and 3.85-4.17 corresponded to —CH (b) and —$CH_2$ (c) groups of epoxy ring. These peaks confirm the formation of epoxidation and the double bond was not affected during epoxidation reaction, and that the desired product was obtained.

Example 4: Synthesis of Resveratrol Glycidyl Ether

Based on the procedure developed for the preparation of epoxy resin from N-coumaroyltyramine, the synthesis of epoxy resin from resveratrol was carried out. Previous attempts to synthesize epoxy resin from resveratrol had resulted in poor yields.

50 grams of resveratrol were placed in a flask under a $N_2$. Epichlorohydrin (202.7 grams) was then added in a 10:1 stoichiometric amount of epichlorohydrin (Epi) to resveratrol at room temperature. They flask was then heated to reflux at 111° C. under slow agitation. Boil while slowly adding NaOH until you reach 3 moles of NaOH/mole of resveratrol (3 functional). This was done by adding 35.0 g. of 20% NaOH solution at a rate of 2.2 ml/minute, following by three further additions of 30.0 g. 20% NaOH solution. The solution was then refluxed for an hour. Excess Epi was then removed from the solution by rotary evaporation (rotovap) distillation at 85° C. 200 mL of methyl ethyl ketone and then 80 ml of 20% NaOH were then added, after which the solution was rinsed and separated. 225 mL of water was then added, after which the solution was rinsed and separated again. Remaining solvent was then removed by rotovap. (if you use acetone, this should azeotrope with water and pull most of that off as well). The final yield was 76.9 grams of resveratrol glycidyl ether.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:
1. A polymer precursor compound according to Formula I or II:

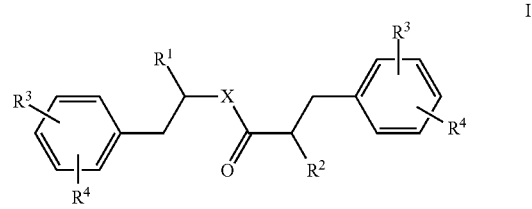

-continued

*(Formula II structure)* wherein R¹ is selected from H and $CO_2R^5$, R² is selected from H and $NHR^6$, R² is a glycidyl ether moiety, R⁴ is a hydrogen or glycidyl ether moiety, R³ is a $C_1$-$C_4$ alkyl ester, R⁶ is an Fmoc or tBoc amine protecting group, and X is selected from O and NH.

2. The polymer precursor of claim 1, wherein R⁴ is hydrogen.

3. The polymer of claim 1, wherein R⁴ is hydrogen and R³ is glycidyl ether moiety in the para position relative to the alkyl group attached to the phenyl ring.

4. The polymer precursor of claim 1, wherein X is NH.

5. The polymer precursor of claim 4, wherein the compound has the structure

*(structure)*

6. The polymer precursor of claim 1, wherein X is O.

7. An epoxy resin prepared from a compound according to Formula I or II:

*(Formula I structure)*

*(Formula II structure)* wherein R¹ is selected from H and $CO_2R^5$, R² is selected from H and $NHR^6$, R³ is a glycidyl ether moiety, R⁴ is a hydrogen or glycidyl ether moiety, R⁵ is a $C_1$-$C_4$ alkyl ester, R⁶ is an Fmoc or tBoc amine protecting group, and X is selected from O and NH.

8. The epoxy resin of claim 7, wherein R⁴ is hydrogen and R³ is a glycidyl ether moiety in the para position relative to the alkyl group attached to the phenyl ring.

9. The epoxy resin of claim 7, wherein X is NH.

10. The epoxy resin of claim 9, wherein the compound has the structure

*(structure)*

11. The epoxy resin of claim 7, wherein X is O.

12. The epoxy resin of claim 7, wherein the epoxy resin is cured.

13. The cured epoxy resin of claim 12, wherein the epoxy resin is cured by forming a copolymer with a hardener.

14. The cured epoxy resin of claim 13, wherein the hardener is an amine curing agent.

15. The epoxy resin of claim 7, wherein the epoxy resin is cured by homopolymerization.

16. A method of making an epoxy resin according to any one of claims 7 or 8 to 11, comprising the steps of:
mixing a reactant according to Formula I or II:

*(Formula I structure)*

*(Formula II structure)* wherein R¹ is selected from H and $CO_2R^5$, R² is selected from H and $NHR^6$, R³ is a hydroxyl moiety, R⁴ is a hydrogen or hydroxyl moiety, R⁵ is a $C_1$-$C_4$ alkyl ester, R⁶ is an Fmoc or tBoc amine protecting group, and X is selected from O and NH, with epichlorohydrin to provide a ratio from 1:1 up to 10:1 epichlorohydrin to reactant, heating the mixture, and reacting the epichlorohydrin with the reactant of Formula I or II by adding from 1 to 3 equivalents of a NaOH solution having a concentration from 1 to 20 weight percent, and purifying the resulting epoxy resin.

17. The method of claim 16, wherein the mixture is heated to a temperature from 70° C. to 90° C. before reacting with epichlorohydrin.

18. A coating composition comprising an epoxy resin according to any one of claims 7 to 11 and an organic solvent.

19. The coating composition of claim 18, wherein the composition further comprises a crosslinking compound.

20. The coating composition of claim 18, wherein the composition further comprises a pigment.

* * * * *